US011229383B2

(12) United States Patent
Pikov et al.

(10) Patent No.: US 11,229,383 B2
(45) Date of Patent: Jan. 25, 2022

(54) METHODS AND SYSTEMS FOR NON-INVASIVE MEASUREMENT OF BLOOD GLUCOSE CONCENTRATION BY TRANSMISSION OF MILLIMETER WAVES THROUGH HUMAN SKIN

(71) Applicants: CALIFORNIA INSTITUTE OF TECHNOLOGY, Pasadena, CA (US); HUNTINGTON MEDICAL RESEARCH INSTITUTES, Pasadena, CA (US)

(72) Inventors: Victor Pikov, Pasadena, CA (US); Peter H. Siegel, La Canada, CA (US)

(73) Assignees: CALIFORNIA INSTITUTE OF TECHNOLOGY, Pasadena, CA (US); HUNTINGTON MEDICAL RESEARCH INSTITUTES, Pasadena, CA (US)

(*) Notice: Subject to any disclaimer, the term of this patent is extended or adjusted under 35 U.S.C. 154(b) by 316 days.

(21) Appl. No.: 14/835,253

(22) Filed: Aug. 25, 2015

(65) Prior Publication Data
US 2016/0051171 A1 Feb. 25, 2016

Related U.S. Application Data

(60) Provisional application No. 62/041,447, filed on Aug. 25, 2014.

(51) Int. Cl.
A61B 5/145 (2006.01)
A61B 5/0507 (2021.01)
(Continued)

(52) U.S. Cl.
CPC ........ A61B 5/14532 (2013.01); A61B 5/0507 (2013.01); A61B 5/01 (2013.01);
(Continued)

(58) Field of Classification Search
None
See application file for complete search history.

(56) References Cited

U.S. PATENT DOCUMENTS 5,657,754 A * 8/1997 Rosencwaig ...... A61B 5/14532
600/316
7,039,446 B2 5/2006 Ruchti et al.
(Continued)

FOREIGN PATENT DOCUMENTS

CN 104013411 A 9/2014
WO 2010/131029 A1 11/2010

OTHER PUBLICATIONS

Jason J. Burmeister, Mark A. Arnold, and Gary W. Small. Noninvasive Blood Glucose Measurements by Near-Infrared Transmission Spectroscopy Across Human Tongues, Diabetes Technology & Therapeutics. Jul. 2004, 2(1): 5-16.*
(Continued)

Primary Examiner — Puya Agahi
(74) Attorney, Agent, or Firm — Steinfl + Bruno LLP

(57) ABSTRACT

A device is described for interrogating human skin using tight coupling between the transmitter and receiver of the millimeter waves (MMWs). Methods are provided to evaluate changes in the amplitude and/or phase of the transmitted MMWs in order to estimate the blood concentration of glucose. Using this device and the related methods, the blood glucose concentration or a change in the blood glucose concentration can be monitored for diagnosing diabetes mellitus and other metabolic disorders of carbohydrate metabolism characterized by either high blood glucose level (hyperglycemia) or low blood glucose level (hypoglycemia), as well as for monitoring (including self-monitoring) a metabolic disorder progression or an efficacy of treatment.

28 Claims, 12 Drawing Sheets

(51) Int. Cl.
A61B 5/00 (2006.01)
A61B 5/021 (2006.01)
A61B 5/01 (2006.01)

(52) U.S. Cl.
CPC ............ *A61B 5/021* (2013.01); *A61B 5/4848* (2013.01); *A61B 5/4866* (2013.01); *A61B 5/7235* (2013.01)

(56) References Cited

U.S. PATENT DOCUMENTS

| | | | |
|---|---|---|---|
| 7,214,190 B1* | 5/2007 | Wilson | A61B 5/05 600/309 |
| 7,371,217 B2* | 5/2008 | Kim | A61B 5/14532 600/309 |
| 7,613,487 B2 | 11/2009 | Shimomura | |
| 8,882,670 B2 | 11/2014 | Hancock | |
| 2002/0169394 A1* | 11/2002 | Eppstein | A61B 5/00 600/573 |
| 2004/0065158 A1 | 4/2004 | Schrepfner et al. | |
| 2005/0254059 A1* | 11/2005 | Alphonse | A61B 5/0066 356/479 |
| 2008/0319285 A1* | 12/2008 | Hancock | A61B 5/05 600/309 |
| 2010/0324398 A1* | 12/2010 | Tzyy-Ping | A61B 5/14532 600/365 |
| 2011/0029049 A1* | 2/2011 | Vertikov | A61B 5/14532 607/104 |
| 2011/0118556 A1* | 5/2011 | Siegel | A61N 5/02 600/300 |
| 2012/0150000 A1 | 6/2012 | Al-Shamma'A et al. | |
| 2012/0310055 A1* | 12/2012 | Jean | A61B 5/0507 600/310 |
| 2013/0001422 A1* | 1/2013 | Lavon | A61B 5/0205 250/338.1 |
| 2013/0289370 A1* | 10/2013 | Sun | A61B 5/14532 600/316 |
| 2013/0289375 A1 | 10/2013 | Fischer | |

OTHER PUBLICATIONS

Yoshio Nikawa, Blood Sugar Monitoring by Reflection of Millimeter Wave, 2007, IEEE, 2007 Asia-Pacific Microwave Conference, pp. 1-4.*
Yoshio Nikawa and Daisuke Someya, Application of Millimeter Waves to Measure Blood Sugar Level, 2001, Proceedings of APMC2001, pp. 1303-1306 (Year: 2001).*
Wahowiak, L., "Blood Glucose Meters. What to look for—and what to know." Diabetes Forecast, Jan. 2013. vol. 66(1): pp. 38-47.
Sacks, D.B., et al., "Guidelines and recommendations for laboratory analysis in the diagnosis and management of diabetes mellitus." Diabetes Care, 2011. vol. 34(6): pp. e61-99.
Vashist, S.K., "Non-invasive glucose monitoring technology in diabetes management: a review." Anal Chim Acta, 2012. 750: pp. 16-27.
Tura, A., "Advances in the development of devices for noninvasive glycemia monitoring: Who will win the race?" NT&M, 2010. 28: pp. 33-39.
Burmeister, J.J. and Arnold, M.A. "Evaluation of measurement sites for noninvasive blood glucose sensing with near-infrared transmission spectroscopy." Clin Chem, 1999. 45(9): pp. 1621-1627.
Kottmann, J., et al., "Glucose sensing in human epidermis using mid-infrared photoacoustic detection." Biomed Opt Express, 2012. vol. 3(4): pp. 667-680.
Guo, X., et al., "Noninvasive glucose detection in human skin using wavelength modulated differential laser photothermal radiometry." Biomed Opt Express, 2012. vol. 3(11): pp. 3012-3021.
Yoo, E.H. and Lee, S.Y., "Glucose biosensors: an overview of use in clinical practice." Sensors (Basel), 2010. vol. 10(5): pp. 4558-4576.
Hofmann, M., et al. "A novel approach to non-invasive blood glucose measurement based on RF transmission." in IEEE MeMeA. 2011. 4 pgs.
Hofmann, M., et al. "Non-invasive glucose monitoring using open electromagnetic waveguides." in European Microwave Conf., p. 546-549, 2012.
Hofmann, M., et al., "Microwave-Based Noninvasive Concentration Measurements for Biomedical Applications." IEEE Trans Microwave Theory Tech, 2013.vol. 61(5): pp. 2195-2204.
Yun, F., et al. "Testing glucose concentration in aqueous solution based on microwave cavity perturbation technique." in Int Conf Biomed Eng Inform. 2010. pp. 1046-1049.
Wang, Q.., et al. "Measuring glucose concentration by microwave cavity perturbation and DSP technology." in Int Conf Biomed Eng Inform. 2010. pp. 943-.
Kim, S., et al., "Noninvasive in vitro measurement of pig-blood d-glucose by using a microwave cavity sensor." Diabetes Res Clin Pract, 2012. vol. 96(3): pp. 379-384.
Melikyan, H., et al., "Non-invasive in vitro sensing of D-glucose in pig blood." Med Eng Phys, 2012. vol. 34(3): pp. 299-304.
Dobson, R., et al. "Blood glucose monitoring using microwave cavity perturbation." Electron Lett, 2012.vol. 48(15): pp. 905-906.
Gennarelli, G., et al., "A Microwave Resonant Sensor for Concentration Measurements of Liquid Solutions." Sensors Journal, IEEE, 2013. vol. 13(5): pp. 1857-1864.
Sharma, N.K. and Singh, S. "Designing a non invasive blood glucose measurement sensor." in IEEE ICIIS. 2012. 3 pgs.
Topsakal, E., et al. "Glucose-dependent dielectric properties of blood plasma." in General Assembly and Scientific Symposium, 2011 XXXth URSI. 2011.
IEEE, IEEE Standard for Safety Levels With Respect to Human Exposure to Radio Frequency Electromagnetic Fields, 3 kHz to 300 GHz. IEEE Std C95.1-2005, ed. C.-K. Chou and J. D'Andrea 2005, Piscataway, NJ: IEEE. pp. 1-238.
Karacolak, T., et al. "Cole-cole model for glucose-dependent dielectric properties of blood plasma for continuous glucose monitoring." Microw Opt Techno Lett, 2013. vol. 55(5): pp. 1160-1164.
So, C.F. et al. "Recent advances in noninvasive glucose monitoring." Medical Devices: Evidence and Research, Dover Press, vol. 5, pp. 45-52, 2012.
Alison, J.M. and Sheppard R., "Dielectric properties of' human blood at microwave frequencies," *Phys. Med. in Biology*, V. 38, pp. 971-978.1993.
Kim, J. et al. "Microwave Dielectric Resonator Biosensor for Aqueous Glucose Solution." Review of Scientific Instruments, vol. 79, No. 1. pp. 086107 1-3. 2008.
Schwerthoeffer, U., et al. "A microstrip resonant biosensor for aqueous glucose detection in microfluidic medical applications." in Biomedical Wireless Technologies, Networks, and Sensing Systems (BioWireleSS), 2014 IEEE Topical Conference on. 2014. pp. 55-57.
Nikawa, Y. and Someya, D. "Non-invasive measurement of blood sugar level by millimeter waves." in Microwave Symposium Digest, 2001 IEEE MTT-S International. 2001. IEEE. pp. 171-174.
Garcia, H.C., et al. "Glucose sensing in saline solutions using V-band waveguides." In Wireless Mobile Communication and Healthcare (Mobihealth), 2014 EAI 4th International Conference on. 2014. pp. 320-323.
Dhakal, R. et al., "Complex permittivity characterization of serum with an air-bridge enhanced capacitor for quantifiable detection of glucose. "Applied Physics Letters, 2015. 106(7): pp. 073702-1-5.
Afroz, S. et al. "Implantable SiC based RF antenna biosensor for continuous glucose monitoring." in SENSORS, 2013 IEEE. 2013.
Chretiennot, T. D. et al. "Double stub resonant biosensor for glucose concentrations quantification of multiple aqueous solutions." in Microwave Symposium (IMS), 2014 IEEE MTT-S International. 2014. 4 pgs.
Siegel, P.H. et al. "Millimeter-wave non-invasive monitoring of glucose in anesthetized rats." in Infrared, Millimeter, and Terahertz waves (IRMMW-THz), 2014 39th International Conference on. 2014. 2 pgs.
Bababjanyan A., et al., Real-time noninvasive measurement of glucose concentration using a microwave biosensor. Journal of Sensors, 2010. 8 Pages.

(56) References Cited

OTHER PUBLICATIONS

Siegel P.H., et al., Noninvasive In Vivo Millimeter-Wave Measurements of Glucose: First Results on Human Subjects, Abstract Submitted to: 42nd International Conference on Infrared, Millimeter, and Terahertz Waves (IRMMW-THz, 2017). 1 page.
Siegel P.H., et al., "Compact Non-lnvasive Millimeter-Wave Glucose Sensor,". Submitted to the 2015 40th International Conference on Infrared Millimeter, and Terahertz Waves (IRMMW-THz, 2015). 3 Pages.

* cited by examiner

METHODS AND SYSTEMS FOR NON-INVASIVE MEASUREMENT OF BLOOD GLUCOSE CONCENTRATION BY TRANSMISSION OF MILLIMETER WAVES THROUGH HUMAN SKIN

CROSS REFERENCE TO RELATED APPLICATIONS

The present application claims priority to U.S. Provisional Patent Application No. 62/041,447, filed on Aug. 25, 2014, the disclosure of which is incorporated herein by reference in its entirety.

TECHNICAL FIELD

The invention relates to a method for measuring blood glucose concentration using non-invasive transmission of millimeter waves through human skin.

BRIEF DESCRIPTION OF DRAWINGS

The accompanying drawings, which are incorporated into and constitute a part of this specification, illustrate one or more embodiments of the present disclosure and, together with the description of example embodiments, serve to explain the principles and implementations of the disclosure.

SUMMARY

Figure 1:
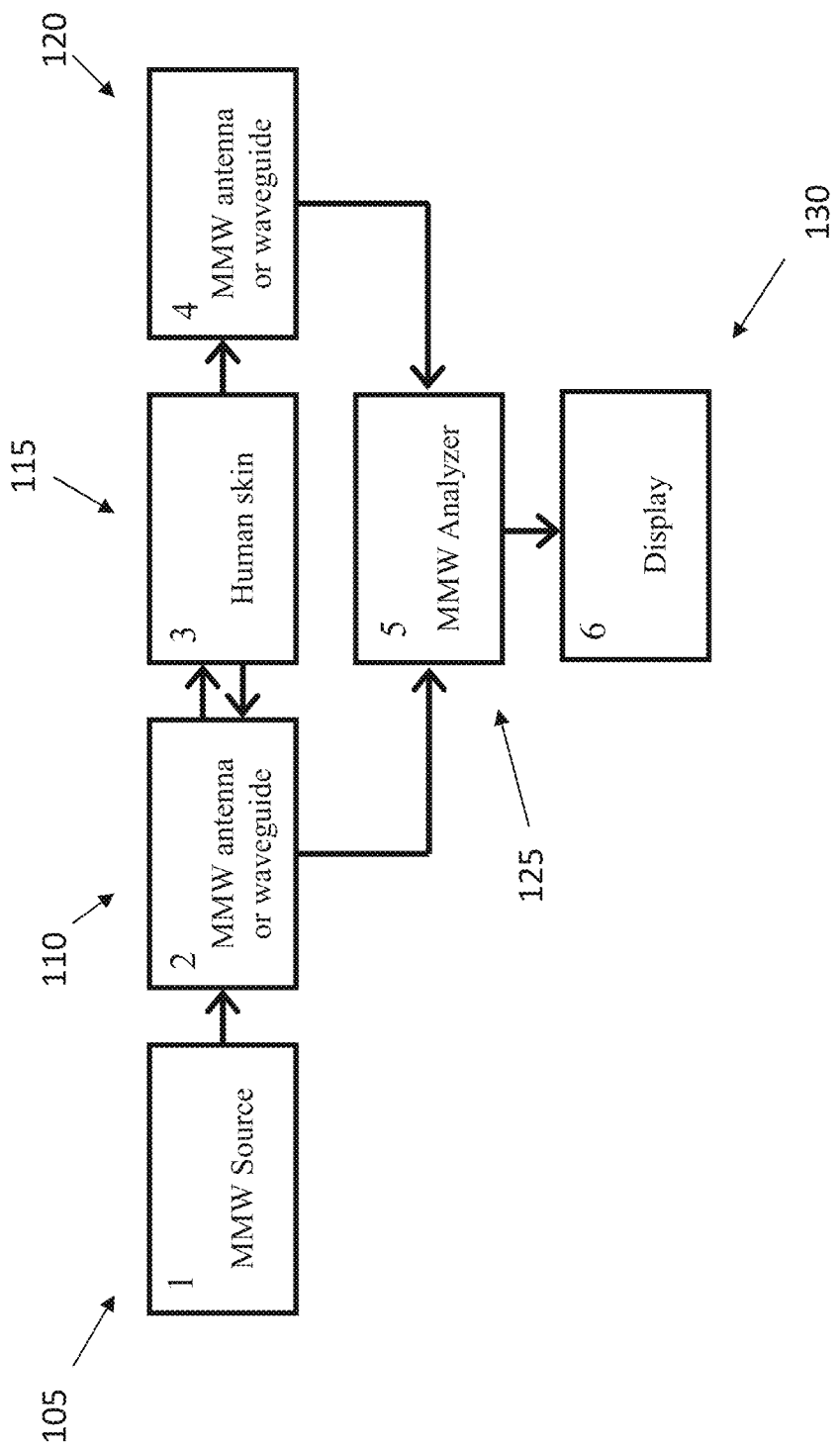
FIG. 1 illustrates a block diagram with elements of the method for performing the non-invasive measurement of glucose concentration by applying MMWs to human skin.

In a first aspect of the disclosure, a device is described, the device comprising: an electromagnetic wave transmitter, configured to be attached to biological tissue and transmit electromagnetic waves through biological tissue; and an electromagnetic wave receiver, configured to receive the electromagnetic waves transmitted through the biological tissue.

In a second aspect of the disclosure, a method is described, the method comprising: applying electromagnetic waves at a frequency in the range of 20 to 300 GHz to biological skin containing blood vessels; receiving the electromagnetic waves transmitted through the biological skin; analyzing the received electromagnetic waves for changes in magnitude or phase; and estimating a chemical concentration or a change in the chemical concentration in blood within the blood vessels, based on the analyzed electromagnetic waves.

BACKGROUND

Measuring glucose is an important medical technique. Glucose is found in blood, tissue, interstitial fluid, intraocular fluid, tears and sweat. Levels in blood may lag levels in interstitial fluids, such as tears, by 5 to 30 minutes. Daily variations result from food intake, circadian rhythm, activity level, temp., etc. Current commercial devices for human blood glucose concentration measurements are invasive. These devices require permanent or temporary embedding under the skin or skin-pricking to draw blood from the subject, see for example Ref. [1]. The discomfort and inconvenience of the invasive approaches lead to poor compliance with the required testing frequency (at least 3 times a day), see Ref. [2]. A noninvasive device for measuring blood glucose would allow more frequent testing, leading to better management of diabetes and other metabolic disorders. Non-invasive measurement of blood glucose concentration has been attempted using visible, near-infrared and mid-infrared light, reverse iontophoresis, electrical impedance (of skin), ultrasound, and electromagnetic waves, see Refs. [3, 4]. Other techniques also include optical polarimetry (measuring the eye) and Raman spectroscopy. However, none of the current non-invasive techniques available have been proven to be effective. The visible and near infrared light approaches have low sensitivity for glucose due to weak glucose absorption, confounding absorption and scattering by other blood and tissue biomolecules, see Ref. [5]. Methods utilizing the transmission of infrared light, e.g. Ref. [6, 7], are preferential to the methods utilizing the reflection of infrared light, as they do not require measuring the spectrum of diffusely reflected light. Nonetheless, the transmission-mode infrared-based techniques for measurement of glucose concentration are vulnerable to high scattering in the tissue and slight changes in the physical position of the source and detector, making it very difficult to separate these artifactual changes from the actual changes in the glucose level. The mid-infrared region (at 9.7 µm) provides a prominent glucose absorption band, but suffers from strong water absorption, limiting the penetration depth to 0.1 mm, see Refs. [8, 9]. The acceptance of the reverse iontophoresis devices has been low due to a commonly observed skin irritation, see Refs. [3, 10]. The electrical impedance and ultrasound devices have been difficult to calibrate, resulting in their poor accuracy, see Ref. [3].

Recently, electromagnetic waves in the microwave and millimeter wave (MMW) regions have been used for measuring blood glucose concentrations in test tubes, see Refs. [11-29]. In all of these studies, a blood sample was taken from the body and placed in a small glass or plastic tube rather than performing the measurements directly in the human subject by transmitting the microwaves or MMWs through the skin. These prior-art approaches cannot be applied for in vivo transdermal measurement of the blood glucose concentration due to low coupling between the transmitting and receiving antennas/waveguides and/or poor sensitivity to changes in glucose concentration. In fact, only changes 10-to-100× greater than the naturally occurring variation in human blood have been observed so far by direct transmission measurements, see Refs. [12-14, 24]. In Refs. [30-33], the proposed methods utilize low frequencies (from 10 MHz to 18 GHz) and a detection mechanism involving a resonant antenna. Design and fabrication of the resonant antenna is tailored to a specific resonant frequency that cannot be tuned, therefore providing a single measurement for a given antenna geometry. Using a single measurement for estimating the glucose concentration makes the resonant antenna method very susceptible to small changes in the device coupling with the skin and to environmental changes at the skin/antenna interface.

DETAILED DESCRIPTION

It has been found that transmission of microwave and millimeter waves (MMW) through biological tissue containing blood vessels alters the magnitude and phase of the MMW signal (see FIGS. 3 and 4, discussed below). The present disclosure describes methods for non-invasive measurement of blood glucose concentration by transmission of MMWs through the skin.

In contrast to known methods, the methods of the present disclosure use low-loss, closely-spaced, tightly-coupled (in the near-field), co-aligned waveguides and/or matched low-loss, high-directivity, tightly-coupled (in the mid-field) antennas straddling thin, loosely-folded skin, ear lobes, skin folds (webbing) between fingers or other regions wherein MMW energy can be easily transmitted non-invasively through the skin tissue. By tight coupling, it is intended herein to mean that the antennas or waveguides in the transmitter and receivers are co-aligned and in close proximity relative to each other. This close physical proximity entails then their electromagnetic coupling. By near-field, it is intended herein to mean that the distance between the antennas or waveguides is less than one wavelength of the electromagnetic waves used. By mid-field, it is intended herein to mean that the distance between the antennas or waveguides is between one and two wavelengths of the electromagnetic waves used. For example, the distance will be less than 1 cm in air for a 30 GHz electromagnetic wave, and even shorter for skin tissue.

Using these methods, the present disclosure describes changes in the transmitted signals with sensitivity sufficient to track glucose level shifts in rodents consistent with normal extremes associated with diabetic monitoring. The non-invasive nature of the proposed methods allows continuous 24-hour tracking of glucose levels in a human subject with the ability to issue a warning whenever the level falls above or below a predetermined threshold. Continuous tracking of glucose levels during different phases of physical activity, mental state, and caloric consumption, allows the device to correlate the glucose metabolism with overall metabolic state of the body. Thus, providing more meaningful analysis of the glucose metabolism and reducing the incidence of false positives and false negatives in issuing the hypoglycemia or hyperglycemia warnings.

Therefore, in some embodiments, the methods of the present disclosure comprise continuously monitoring (over the course of many days, for example, at least seven days) an individual's microwave absorption signature (collecting data every few minutes), and then correlate glucose levels directly with an absolute scale (such as a blood test) in order to fully characterize the normal range of microwave signatures for each person, individually. In this way, it is possible to evaluate changes from the normal range, even under unusual circumstances or for individuals that do not fall within an established range. This will allow a reduction of false positives and tailoring of the sensor to fit specific individual lifestyles and daily variations.

The methods of the present disclosure calculate the glucose concentration based on averaging over a wide range of frequencies (e.g. 35-39 GHz for the CMOS device and 27-40 GHz for the waveguide demonstration), thus reducing the effects of frequency mismatch and time-varying changes in coupling. Another difference from previously proposed methods is the built-in source and detection circuits and smaller transmit/receive elements for the proposed shorter wavelengths, jointly allowing a high degree of miniaturization to be implemented. Additionally, the methods of the present disclosure use the changes in the whole received electromagnetic signal rather than in a small portion of the signal, such as in the case for the methods using a resonant antenna, due to its high quality factor (Q factor). The methods of the present disclosure also allow tailoring the frequency, sensitivity, bandwidth, and power level to match the particular subject or application without having to change the antenna geometry or placement.

In one embodiment of the present disclosure, a method is described for diagnosing diabetes mellitus and other metabolic disorders of carbohydrate metabolism, characterized by either high blood glucose level (hyperglycemia) or low blood glucose level (hypoglycemia). The method can comprise: applying MMWs at a frequency in the range of 20 to 300 GHz using a first (transmitting) waveguide applied to the skin of a subject, in an amount sufficient to penetrate full thickness of the tissue and be detected by the second (receiving) waveguide; measuring the signal magnitude and phase changes of the received MMWs; and diagnosing the metabolic disorder based on estimated blood glucose level. In several embodiments of the method, the applying of the MMWs can comprise applying several MMW amplitudes, base frequencies, or modulation frequencies, or applying MMWs in a duty cycled manner. The skin target, in several embodiments, can be on the ear, neck, arm, leg, or other parts of the body, or a combination thereof.

In another embodiment of the present disclosure, a method of monitoring (including self-monitoring) a metabolic disorder progression or an efficacy of treatment is provided. The method can comprise: applying MMWs at a frequency in the range of 20 to 300 GHz using a first (transmitting) waveguide or integrated planar antenna applied to the skin of a subject, in an amount sufficient to penetrate full thickness of the tissue and be detected by the second (receiving) waveguide or integrated planar antenna; measuring the signal magnitude and phase changes over time for the received MMWs; administering glucose or a drug for a metabolic disorder to the subject; and monitoring a metabolic disorder progression or an efficacy of treatment based on an estimated change in the blood glucose level over time. Examples of drugs include, but are not limited to, quick-acting and long-acting insulins, sulfonylureas, alpha glucosidase, synthetic amylins, DPP-IV inhibitors, biguanides, sodium-glucose co-transporter 2 inhibitors, angiotensin-converting enzyme inhibitors, and angiotensin receptor blockers. In several embodiments of the method, the applying of the MMWs can comprise applying several MMW amplitudes, base frequencies, or modulation frequencies, or applying MMWs in a duty cycled manner. The skin target, in several embodiments, can be the ear, neck, arm, leg, or other parts of the body, or a combination thereof. A particularly prescient and widespread application for the methods of the present disclosure is the monitoring of patients during sleep, since these techniques do not perturb sleep and can detect changes in blood glucose level requiring a doctor's or nurse's attention. No other known techniques can be used in a similar non-invasive way for continuous monitoring of glucose.

In several embodiments, the MMWs can: be applied in the range from 20 to 300 GHz, either fixed or tunable; be applied as a continuous wavelength (CW) or pulsed; be modulated from 0 to 100 MHz; have an incident power density of within specified MPE (maximal permissible exposure) of 1 mW/cm$^2$ such as, for example, in Ref. [34], or a combination thereof; be applied until they exceed a predetermined upper MMW exposure limit, such as the specific absorption rate of 1 W/kg; be applied as several amplitudes; be applied in a duty cycled manner, for example, by interrupting MMW exposure for a predetermined time interval, and resuming the exposure after the predetermined time interval. The operating parameters of the MMW exposure system can be set according to the specific characteristics, described above, of the MMWs.

Referring to FIG. 1, a MMW source (105) is used to generate the MMW energy for transmission through human skin. The MMW source can be a device known in the art, such as, for example: a backward-wave oscillator, orotron, Gunn diode oscillator, IMPATT Diode, Solid State Gunn Diode, synthesizer and upconverter, oscillator and discrete or MMIC amplifier, silicon or silicon germanium CMOS oscillator and power amplifier, YIG tuned oscillator, dielectric resonator, vacuum tube oscillator, clinotron, gyro-klystron, gyrotron, traveling wave tube, gyro traveling wave tube, or pulsed magnetron. In some embodiments, the control unit can be housed together with a power supply for providing power to, for example, the MMW source and an amplifier. In other embodiments, the power supply can be housed separately from the control unit.

FIG. 1 illustrates elements of the method for performing the non-invasive measurement of glucose concentration by applying millimeter waves (MMWs) to human skin.

Referring to FIG. 1, the MMW antennas or waveguides (110, 120) can be devices known in the art, such as, for example: a planar or 3D waveguide, direct source to antenna coupled radiators, planar antenna coupled oscillators and amplifiers, wire or planar rectenna or any known source-coupled RF radiator. As known to the person of ordinary skill in the art, a rectenna is a rectifying antenna, a type of antenna that is used to convert MMW energy into direct current electricity. Rectennas are used in wireless power transmission systems that transmit power by radio waves.

The antenna or waveguide (110) can be used for transmitting the MMWs into the skin, while the antenna or waveguide (120) can be used for receiving the MMWs after passage through the skin.

The delivery device can be single or multimode, rectangular, round, square, ridge, elliptical, or the like. In some embodiments, the MMW antennas or the MMW waveguides can be used for direct skin contact or for non-contact application, being separated from the skin by a layer of clothing or another dielectric. The first MMW antenna/waveguide (110) can be connected to the MMW source (105) and is used for transmitting the MMW energy, while the second MMW antenna/waveguide (120) is used to receive the MMW energy transmitted through the human skin (115). The MMW waveguides and antennas can be either planar or three-dimensional in structure. In some embodiments, the same antenna or waveguide can be used for both receiving and transmitting MMWs. An analyzer (self-mixing or heterodyne MMW detector) (125) can be used to analyze MMWs, either before transmission or after reception. Results from the analyzer (125) can be displayed on a display, for example (130).

Figure 2:
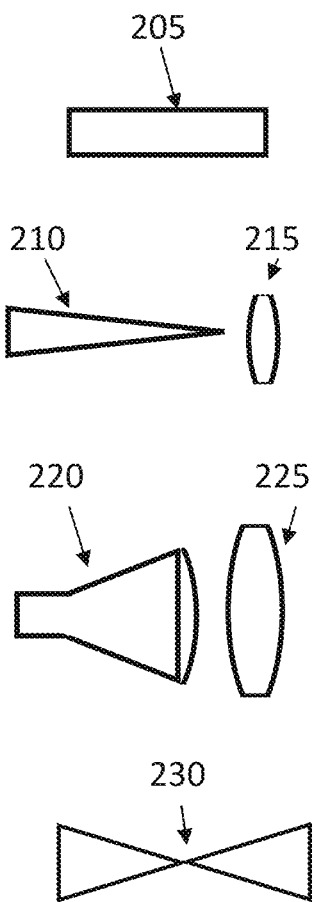
FIG. 2 illustrates various embodiments of the MMW antenna/waveguide for the non-invasive measurement of glucose concentration system.

Referring to FIG. 2, which illustrates some embodiments of the present disclosure, MMW waveguides can take the form of simple 3D open ended structures (hollow or dielectrically loaded) (205), or conical (210), pyramidal (220) or ellipsoidal horns. Also referring to FIG. 2, MMW antennas can be single wire or multi-wire antennas, or planar shaped dielectric backed antennas (230). The planar antennas can be made, for example, from a polymer substrate, such as polyimide, LCP, polytetrafluoroethylene, SU-8 photoresist, polyethylene, polypropylene, TPX, polystyrene, or parylene. The planar antennas can be manufactured, for example, using different metal machining or lithographic technologies known in the art, such as for example: nanoimprint lithography (either thermoplastic/hot embossing or photo/UV-based), optical lithography, electron beam lithography, X-ray lithography, or synchrotron radiation etching. These planar substrates can be patterned with metal features, using different microfabrication procedures known in the art, such as for example: electroplating, liftoff, spinning, plasma etching, sputter deposition. Single or multiple layers of polymer substrates and metal patterns can be used in combination. The MMW antenna/waveguide can be coupled to the skin through an optional beam shaping element that can comprise for example convex, concave, or collimating lenses (215, 225) or spherical, parabolic, elliptical or conical minors, optionally movable for depth and lateral focusing.

FIG. 2 illustrates various embodiments of the MMW antenna/waveguide for the non-invasive measurement of glucose concentration system. The first MMW antenna/waveguide is connected to the MMW source and is used for transmitting the MMW energy, while the second MMW antenna/waveguide is used to receive the MMW energy transmitted through the human skin.

In some embodiments, the system can also comprise, for example: a capacity for detecting local temperatures by radio frequency (RF) or optical (visible, infrared) thermometry; a capability for detecting tissue pressure using piezoelectric or ultrasound sensors; a capability to tune the applied power, frequency, modulation, and localization of applied irradiation; a telemetry circuit for wireless communication with an external controller/programming device; or a combination thereof. In addition, MMWs can be delivered either automatically through a pulse generator built into the stimulation system, or using commands from an external controller that can communicate with the stimulation system.

The system can include a safety protection feature that discontinues MMW stimulation in the event that the MMWs are applied in a manner that exceeds a safety limit. Safety limits can be defined based upon the output of the MMW source (such as the incident power density within specified MPE of 1 mW/cm$^2$, as in Ref. [34], or the specific absorption rate within 1 W/kg) or upon the detection of physiological responses (body temperature, blood pressure rate, blood oxygenation, respiration) exceeding the normal limits.

The present disclosure may be better understood by referring to the accompanying examples, which are intended for illustration purposes only and should not in any sense be construed as limiting the scope of the invention.

EXAMPLE 1

With reference to the changes in the MMW signal during transmission through the human tissue containing blood vessels, both MMW magnitude and phase may be altered by blood glucose concentration. Such a method could be used for non-invasive diagnosis and monitoring of treatment in various metabolic disorders of carbohydrate metabolism characterized by either high blood glucose level (hyperglycemia) or low blood glucose level (hypoglycemia). At low MMW power, the MMW magnitude and phase transmitted through the rat's ear were differentially altered by intraperitoneal injections of physiologically-relevant doses of insulin and glucose but not by equivalent saline injections.

Materials and Methods

In this example, the applied MMW energy was irradiated from one open-ended unloaded single-mode waveguide into another waveguide. With reference to FIG. 3, both waveguides had a rectangular aperture (7.112×3.556 mm) and were loosely (without constricting) clamped together around a rat's ear using a small magnet (305). The small gap between the two waveguides enabled strong coupling of MMWs from the transmitted waveguide, through the ear, and into the receiving waveguide with minimal MMW leakage to the sides. The MMW power was directed perpendicular to the ear to give the strongest and most uniform coupling of transmitted power. Reflected MMW energy from the transmitting waveguide was collected and measured simultaneously with the transmitted MMW energy using a standard commercial 2-port MMW network analyzer. The MMW source was operated in continuous wave mode at 25% duty cycle (a 7-sec long on-period followed by a 21 sec-long off-period). The MMW frequency was swept from 27 to 34 GHz, and the power levels at the output of the waveguide were measured to be 1.5 mW across the band. Using the published data for the same frequency, similar tissue and a Beer's law ($I=I_0 e^{-\alpha x}$) for the intensity drop with penetration depth x, it was estimated that the loss tangent for MMW absorption by skin was 1.48, translating into the absorption coefficient of 52 $cm^{-1}$, and power drop of 99.5% at 1 mm. Using a further approximation that the energy in the MMW beam is uniformly distributed over the tissue within the half-power ellipse, the maximal power of 1.5 mW exiting the waveguide port produces an incident power density of approximately 6 $mW/cm^2$ incident on the skin surface. Since the reflection coefficient on the skin at these wavelengths was measured to be approximately 90%, only 0.6 $mW/cm^2$ of the MMW power is transmitted into the skin, which is 1.7 times lower than the most conservative current safe exposure level of 1 $mW/cm^2$ according to Ref. [34].

Figure 3:
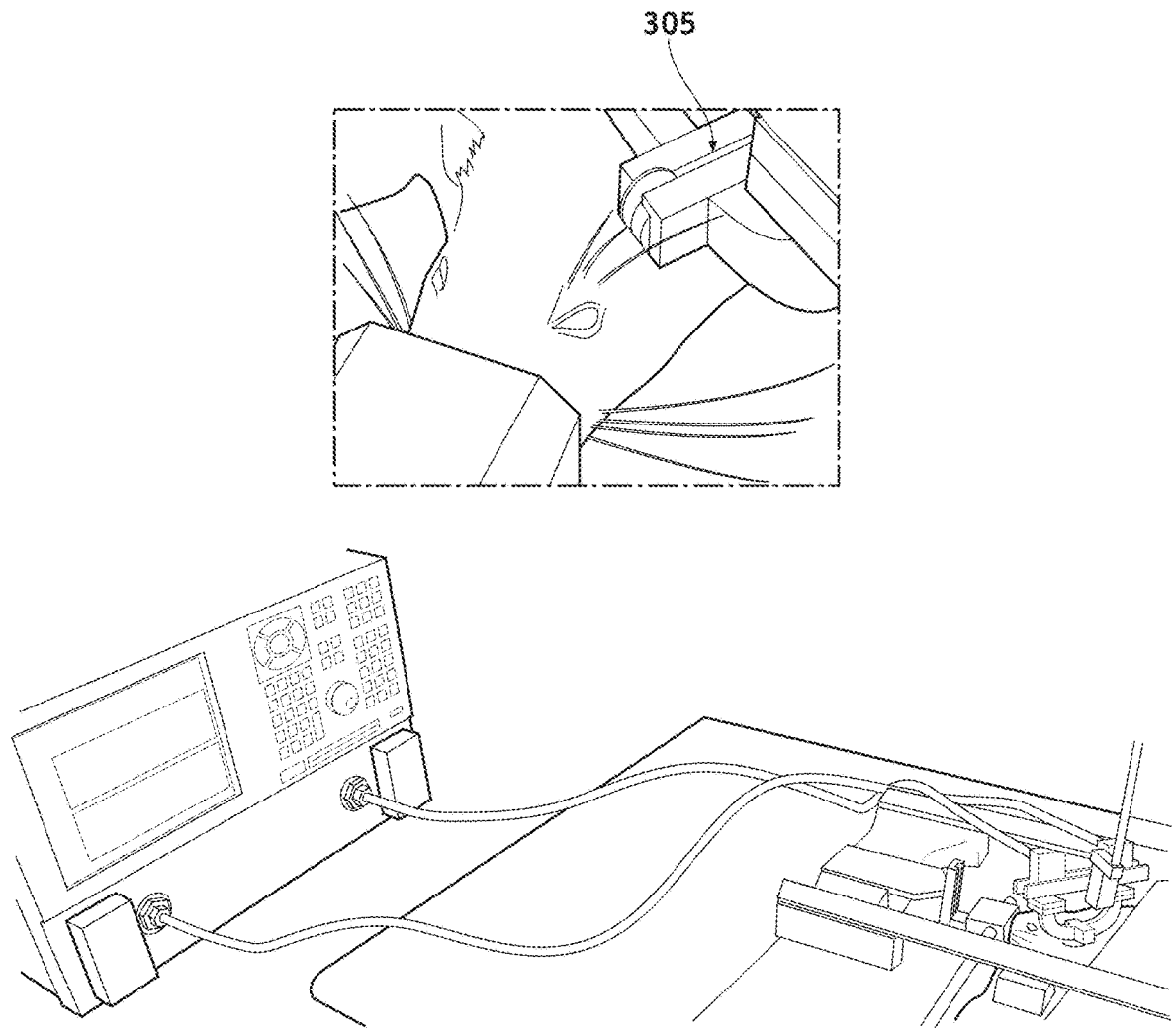
FIG. 3 depicts a sample setup for MMW transmission through a rat's ear.

FIG. 3 illustrates a sample setup for MMW transmission through a rat's ear. The rat's left ear is loosely clamped between two rectangular waveguides held in position by small magnets embedded in the flanges. The waveguides are coupled to the coaxial cables for connection with the vector network analyzer (E8363B, Agilent).

Results

Following the intraperitoneal injection of glucose (2 g per kg of body weight), we observed a 0.2 to 0.25 dB increase in the MMW power transmission (i.e. lower absorption loss) across all examined frequencies from 27 to 34 GHz. This is consistent with Cole-Cole models predicting a decrease in conductivity of blood with increasing glucose levels as in Ref. [35], and hence a decrease in the MMW power absorption. In contrast, following the intraperitoneal injection of insulin (2 U per kg of body weight), a 0.1 to 0.15 dB decrease in the MMW power transmission (i.e. higher absorption loss) was observed across all examined frequencies (see FIG. 4).

Figure 4:
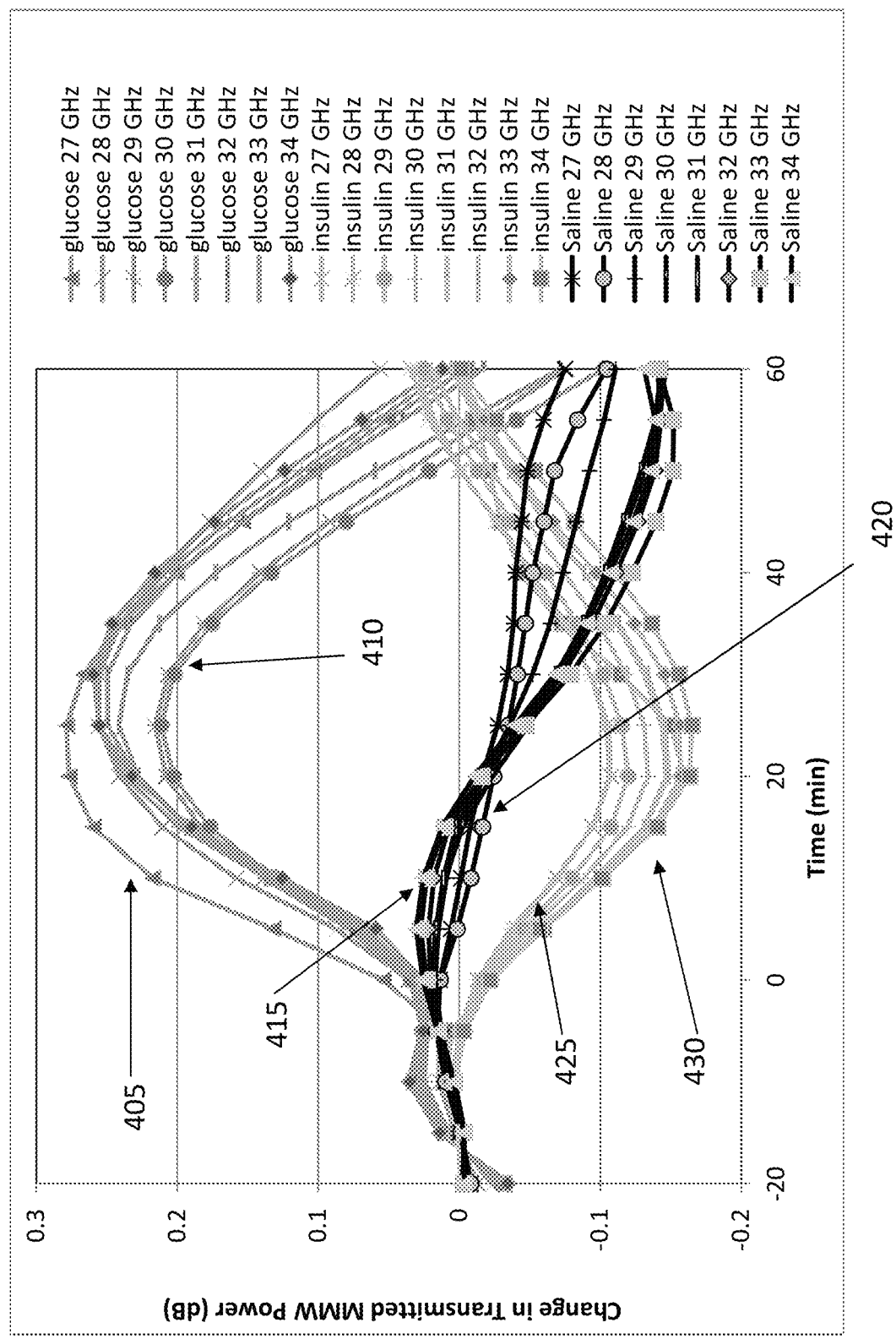
FIG. 4 illustrates a panel of representative changes for the MMW power transmitted through the rat's ear following the intraperitoneal injections of glucose, insulin, and saline solution.

With reference to FIG. 4, curves grouped between (405) and (410) refer to injection of glucose at different frequencies, curves grouped between (415) and (420) refer to injection of saline at different frequencies, and curves grouped between (425) and (430) refer to injection of insulin at different frequencies.

As visible in FIG. 4, the MMW power transmission changes peaked at 20-30 minutes post-injection, consistent with the absorption rate of glucose and insulin from the peritoneal cavity into the blood stream. Since both the glucose and insulin were dissolved in saline, the possibility of non-specific effect from intraperitoneal injection was examined with an equivalent amount of saline (0.5 ml). At 20-30 min post-injection, a less than 0.05 dB decrease in the MMW power transmission was observed. Therefore, neither the effect of glucose injection nor the effect of insulin injection can be fully reproduced by a non-specific action of saline. In summary, the experimental data from the rat's ear provide a strong support for specificity of changes in the MMW power transmission during experimental manipulation of the blood glucose concentration. This example provides the first example of using the MMW transmission through the skin for directly measuring the blood glucose concentration changes.

FIG. 4 illustrates representative changes in the MMW power transmitted through the rat's ear following the 0.5 ml intraperitoneal injections of glucose (1 g/kg, blue lines), insulin (2 U/kg, green lines), and saline (0.9%, black lines). The MMW frequencies range from 27 to 34 GHz. The injections were performed at 0 min time-mark.

EXAMPLE 2

In a clinical setting (e.g. at a hospital bed side), a patient receiving the nutrients through an intravenous glucose line is equipped with a MMW glucose-sensing device operating at 20 to 300 GHz. The blood glucose concentration is recorded with the device for continuous monitoring of the patient's metabolic state.

Figure 5:
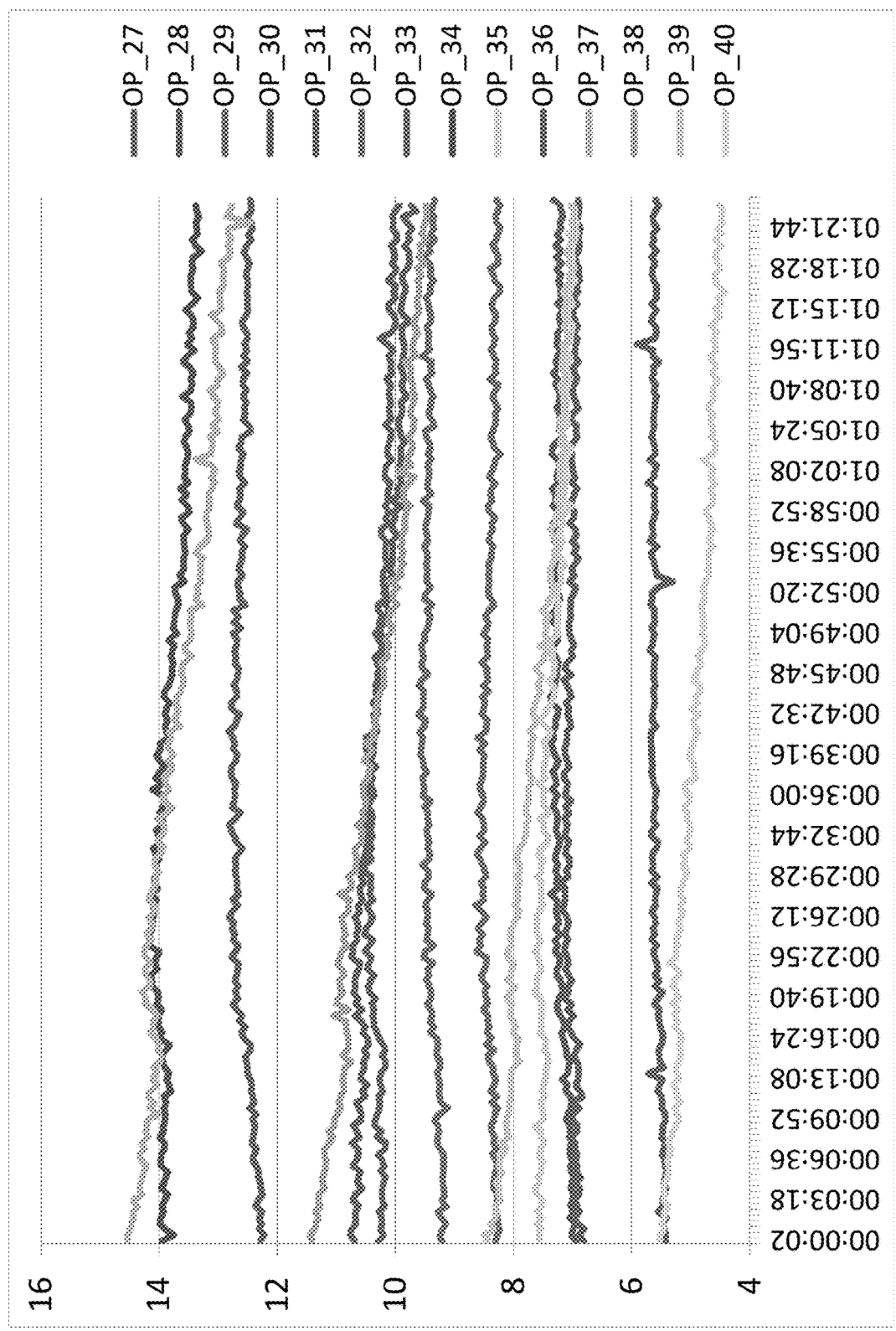
FIG. 5 illustrates exemplary raw data.

In experiments measuring glucose with the methods of the present disclosure, in some embodiments the measuring apparatus comprised a HP83650 with 83554A X2 doubler head generating up to 280 uW or 2.2 $mW/cm^2$ RF power at the ear; a diode detector with a DC amplifier with a sensitivity of 275 uW/V. The power loss measuring through a rat ear was about 18 dB. The diode detector (0.1-50 GHz, Agilent 8474E) was attached to a Ka band waveguide-to-coax transition. Input was via coaxial cable from the 83554A into Ka band coax-to-waveguide transition and Ka band rectangular waveguide. FIG. 5 illustrates exemplary raw data captured with the measuring apparatus (trans. amp vs time and frequency).

Figure 6:
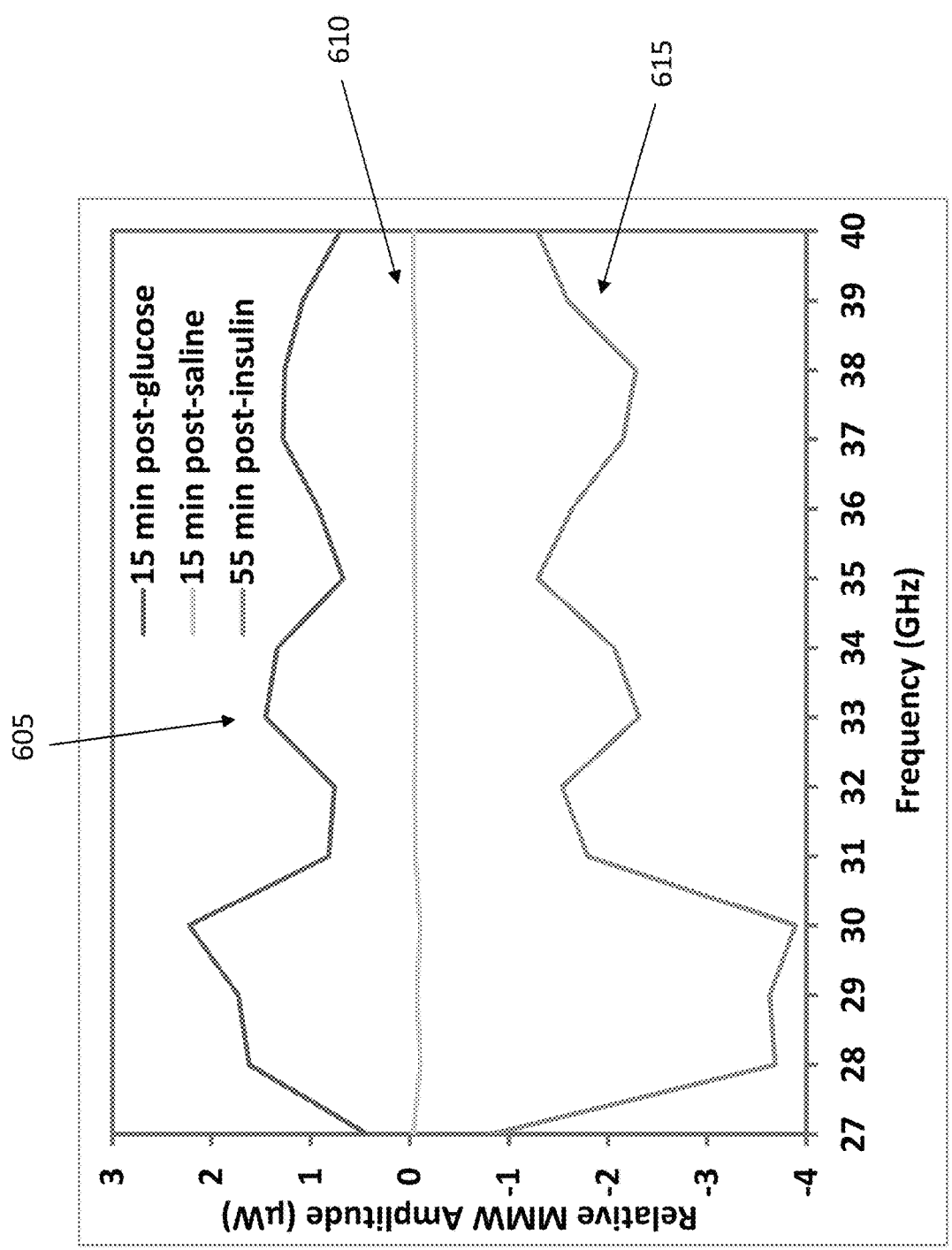
FIG. 6 illustrates an exemplary measurement.

FIG. 6 illustrates the measurements of changes in MMW transmission through rat ear with a clear distinction between signals originating from glucose (605), saline (610) or insulin (615). The frequency-dependent variations in the graph of FIG. 6 represent the standing wave in the waveguides of the measuring apparatus.

In FIG. 6, the power levels are calculated from raw voltage measurements using the detector calibration factor (approximately 0.28 mV/uW). The signals collected after 0.5 ml injections of following solutions: 1 g/kg glucose, 2 U/kg insulin, and 0.9% saline. Measurements were taken with a network vector analyzer Anritsu 37397C with a Ka band waveguide magnetically clamped around a sealed 10 ml fluid chamber (OptiCell, Thermo Fisher Scientific, Rochester, N.Y.). Additional details of the measurement setup are described in Ref. [36]. Similar results were obtained, when measuring saline versus glucose plus glucose solutions in vitro in Ref. [25].

Figure 7:
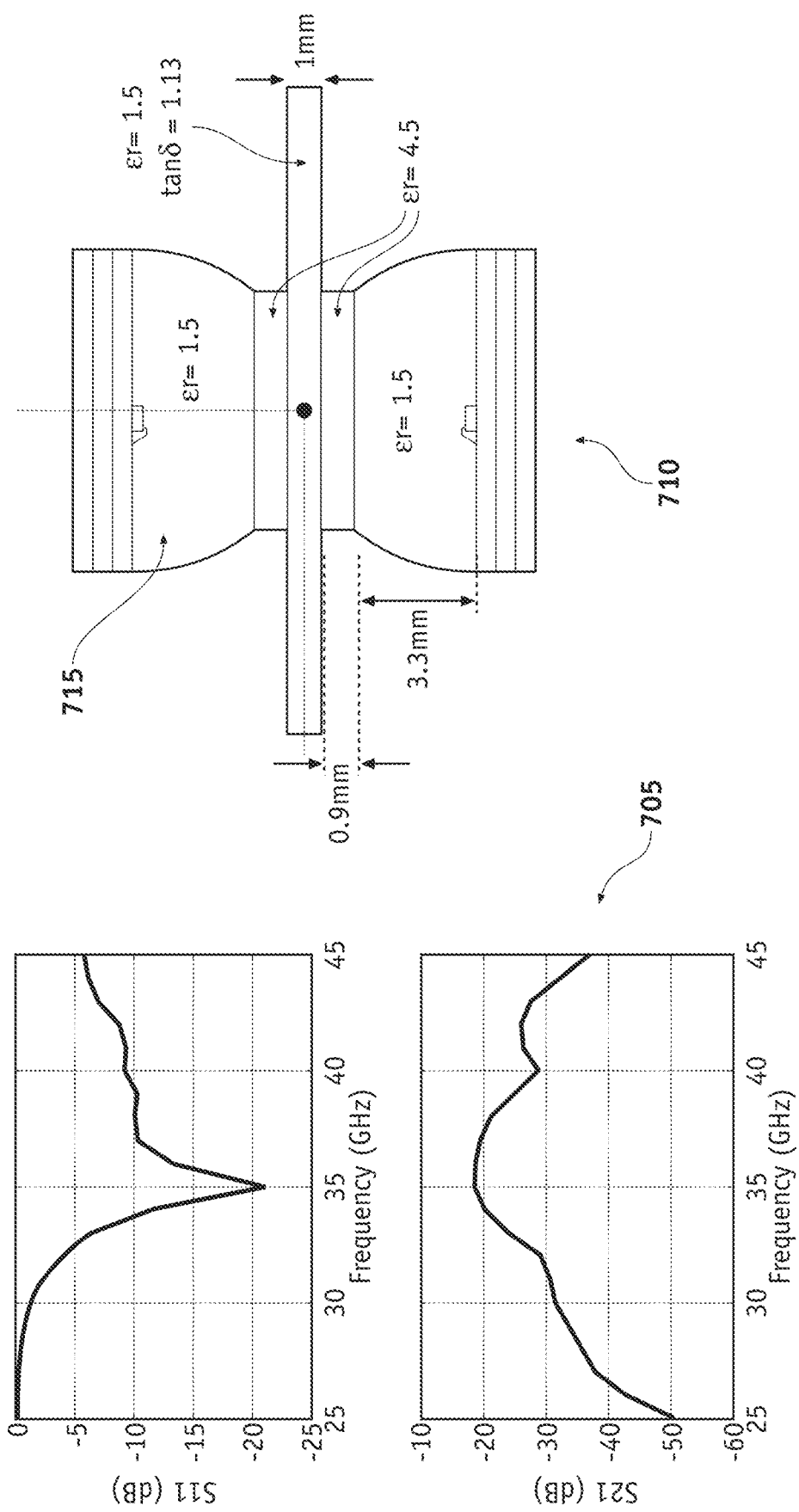
FIG. 7 illustrates exemplary simulations of glucose measurements.

FIG. 7 illustrates exemplary simulations of glucose measurements according to the methods of the present disclosure. Plots (705) shows transmission and reflection vs. frequency for the circuit structure (710). Nominal bandwidth was 35-39 GHz. HFSS simulation set up (710) comprises front/front antennas and surrounding media during measurements. Biological tissue is assumed to be 1 mm thick with a Kapton matching layer on chip. Capture gel was Locktite 349 (715, $\epsilon_r$=1.5), while the antenna is a folded dipole on 4 layer PCB (stacked Rogers 4350B) with $\epsilon_r$=3.5. The antenna ground plane is 1 mm below the top surface.

Figure 8:
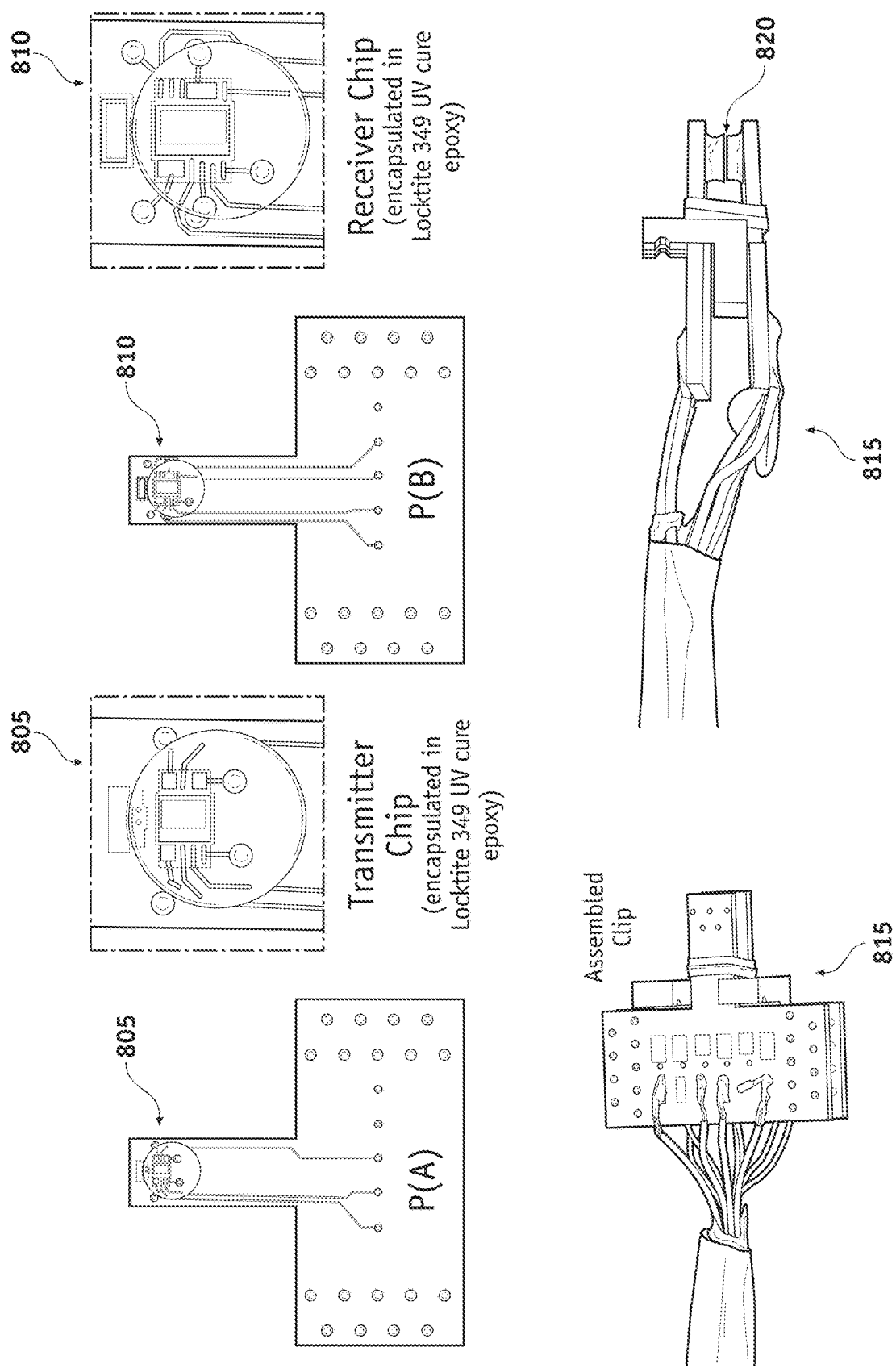
FIG. 8 illustrates exemplary transmitter and receiver chips.

FIG. 8 illustrates exemplary transmitter (805) and receiver (810) composed of monolithic silicon CMOS MMW transmit and receive integrated circuit chips coupled with a highly directive radiating antenna element. These chips are assembled together using a flexible soft-clamping coupling clip. The measuring area is visible in (820). In this embodiment, the chips are encapsulated in Locktite 349 UV cure epoxy. In this embodiment, RF power on chip was about 5 mW, while radiated power was about 0.5 mW. Detection was by self-mixing (not via heterodyne process), and a signal to noise of approximately 15 dB was measured after transmission through the skin fold between the thumb and the index finger. This is sufficient to measure signal levels through the skin folds between other fingers or the ear lobe. The compact closely-spaced, and tightly-coupled antenna configuration is unique and the first implementation of this circuit concept in silicon CMOS. Unique feature of this design, in contrast to the use of resonant antennas, is that the electromagnetic wave can be electronically tuned from 35 to 39 GHz. The current configuration uses wired connections for signal control and data output, but can readily be configured with wireless control and wireless data transmission to an electromagnetic wave analyzer. Additional signal gain of more than 10,000 can be implemented by using a heterodyne receiver configuration rather than a self-mixing detector utilized in the current configuration.

Several in vitro measurements, such as those described above, show that MMW permittivity changes caused by physical parameters (hydration, temperature, chemical composition etc.) are large enough to be detected both in skin and in blood with Tx/Rx techniques.

Frequency can be selected based on: sampling area, penetration into the skin, reflection coefficient, absorption loss, absolute value of the permittivity or conductivity, sensitivity to hydration, and style of measurement.

Results on anesthetized rats show that changes in in vivo glucose concentration are directly correlated with changes in MMW transmission through the skin at incident power levels within the safe limits for humans (1 mW/cm$^2$ for 6 minutes).

In vitro studies of saline and saline plus sugar solutions show that measured changes in absorption and reflection correlate directly with changes in sugar concentration and follow the same inverse relation: increasing sugar (glucose) =decreasing absorption.

The positive results of these experiments allow the design of a simple direct detection Ka band CMOS transceiver chip set to demonstrate a practical monitoring instrument. Subsequent testing can focus on showing that: MMW absorption is not sensitive to changing skin conditions sweating, hydration levels, temperature, ointments and contaminants etc.; MMW transmission changes are specific to the blood glucose level, or at least related to the glucose metabolism or other metabolic processes including the breakdown of fatty acids and proteins; Diurnal changes in signal levels that are not directly related to glucose concentration, can be properly subtracted out using continuous monitoring and individually established baselines. In other embodiments, if additional sensitivity is required, a full heterodyne detection scheme can be used, with an improved additional 40 dB of signal to noise ratio.

Figure 9:
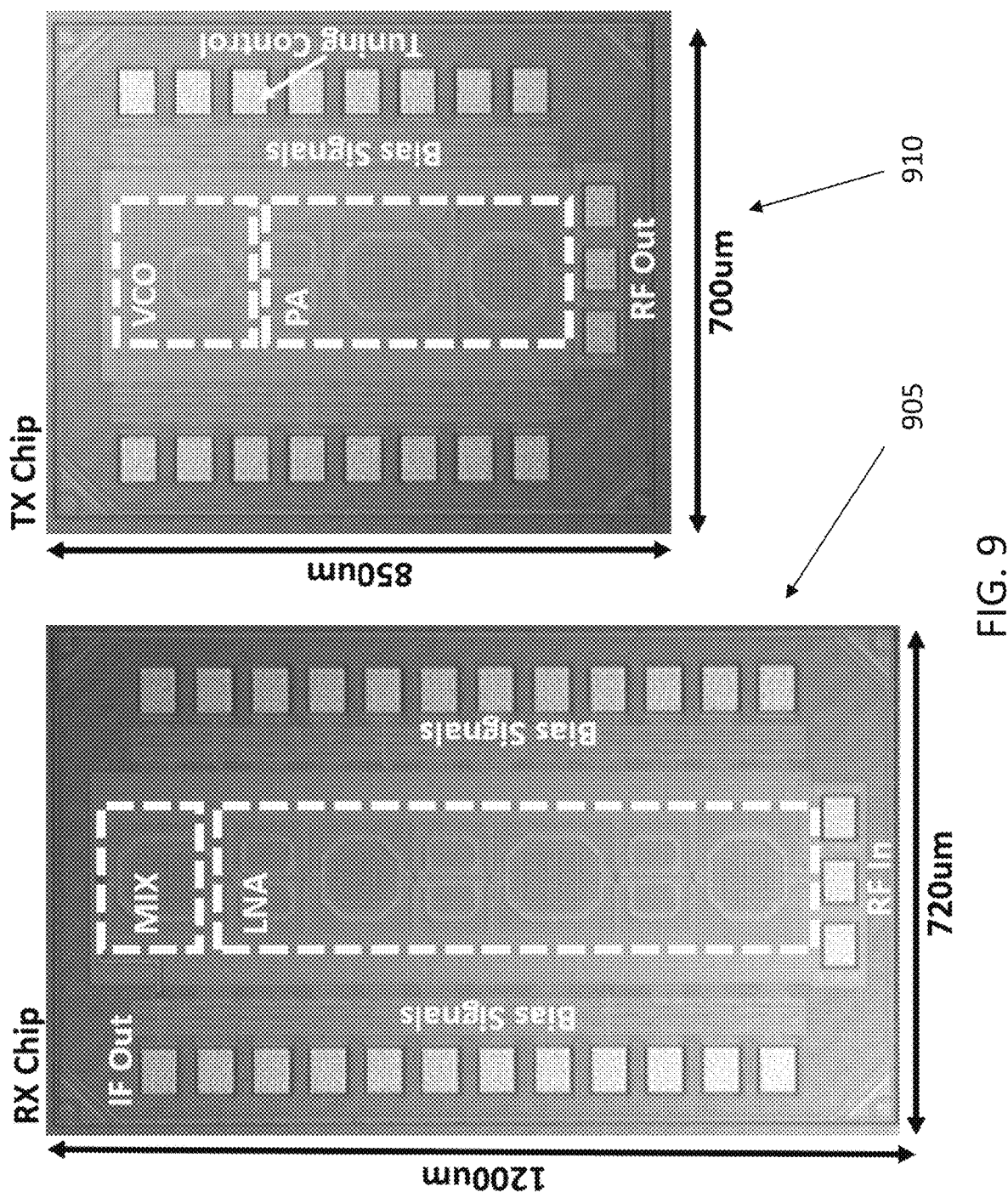
FIG. 9 illustrates die photographs of exemplary transmitter and receiver chips.

FIG. 9 illustrates die photographs of exemplary transmitter (910) and receiver (905) chips with overall dimensions in microns. In some embodiments, the transmitter is designed to generate up 3.1 mW of tunable RF CW energy between 33 and 37 GHz. The receiver uses a non-coherent self-mixing detection circuit with an input referred detection limit of 1 nanowatt (−60 dBm). The expected loss through the tissue is between 20 and 30 dB, leaving plenty of detection headroom even at 1 mW/cm$^2$ input power density providing a final signal to noise of 30-40 dB. When higher losses are encountered the gain can be increased substantially by reducing the transmitter duty cycle without exceeding any SAR safe limits in the tissue. Modulation is applied to the transceiver through a standard TTL input port.

Figure 10:
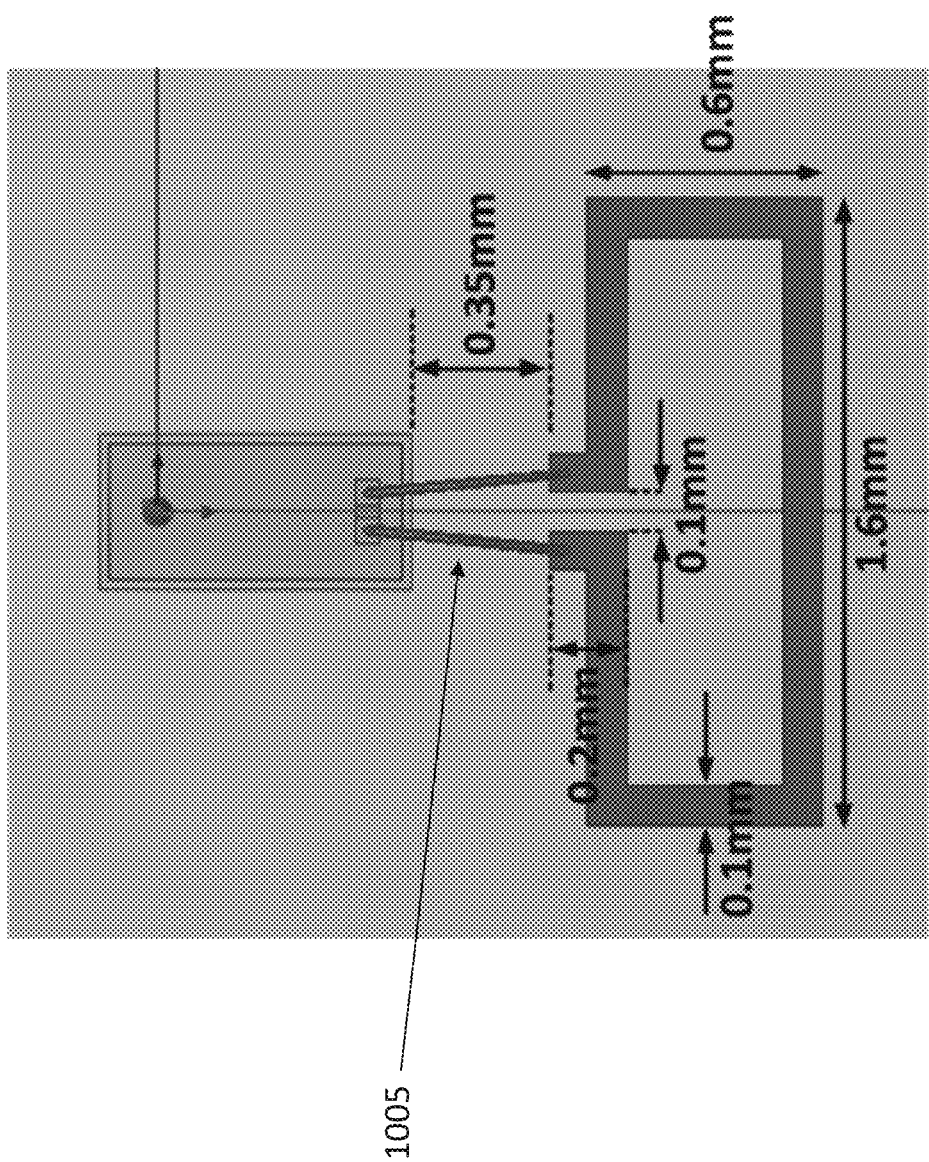
FIG. 10 illustrates an exemplary antenna attached to a chip.

In some embodiments, The transmit and receive chips are integrated onto the ends of separate printed circuit boards (PCB) composed of a 1.5 mm thick RO4350B/bondply sandwich. Appropriate dielectric and metal ground plane regions are pre-etched into the PCB. Each RFIC must be coupled to an RF antenna that can radiate into the tissue (transmitting antenna) and pick up the power on the other side (receiving antenna). A small folded dipole was designed and placed on the PCB close to the RFICs and coupled to the output/input port via short wire bonds (1005, as visible in FIG. 10).

In some embodiments, the power, data and control tabs on each RFIC are wire bonded to pads that lead to a small 10 pin connector on the opposite end of the PCB. The antenna and RFICS are then coated with a BCB protection layer (Dow Chemical). Matching to the tissue is accomplished by sanding the BCB layer down to a flat half-wavelength thick sheet and then adding (gluing) a quarter wavelength thick matching layer composed of low loss glass on top. A diagram of the antenna structure and EM simulation results using HFSS showing the predicted power transfer characteristics through 1 mm of tissue are given in FIG. 7.

Figure 11:
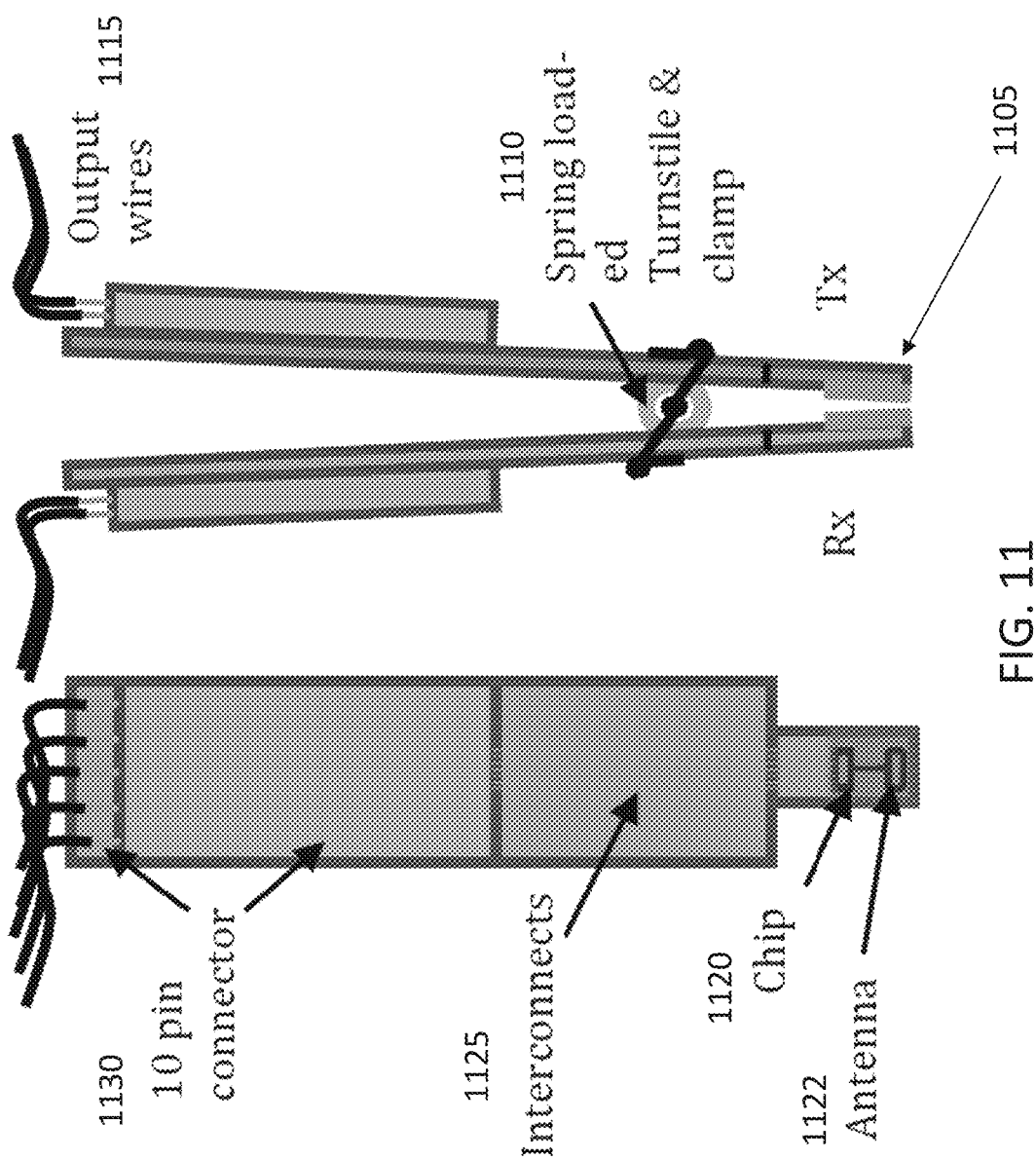
FIG. 11 illustrates an exemplary clamp transceiver.

In some embodiments, the two PCBs are tied together in a clothes-pin type of arrangement using rubber bands and a small cylinder as a pivot for the clamp (FIG. 11). Once in place the antennas are in intimate contact with the tissue on both the transmitter and receiver sides, and continuous measurements can be performed on either animals or humans while the subjects are in an active state. In some embodiments, the wire tether can be replaced by a battery and wireless transceiver system.

In some embodiments, the transceiver chip operates at a frequency between 35 and 39 GHz.

As visible in FIG. 11, in some embodiments the receiver and transceiver chips form the two sides of a clamp (1105), whose tension is regulated by for example a spring (1110). Wires (1115) can connect the measuring probe to the rest of the system. Antennas (1122) and related chips (1120) are joined by interconnects (1125) and a connector, for example a 10 pin connector (1130).

Figure 12:
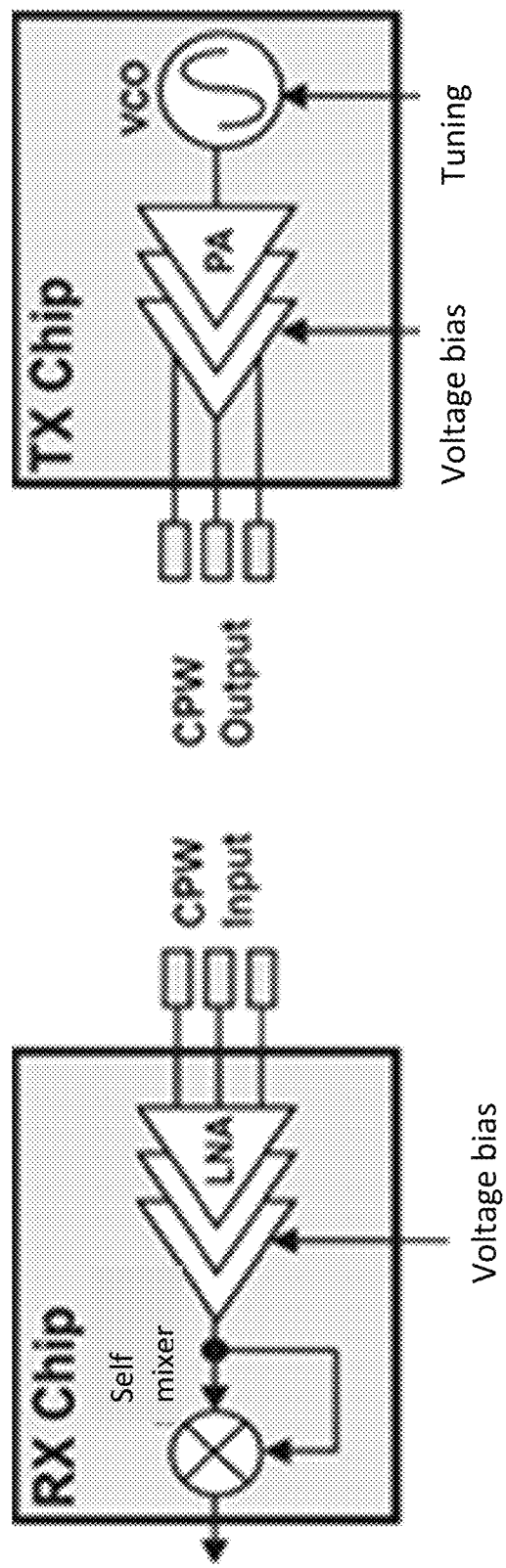
FIG. 12 illustrates a block diagram of an exemplary millimeter wave (35-39 GHz) CMOS transceiver.

With reference to the exemplary transmitter and receiver chips of FIG. 9, FIG. 12 illustrates an exemplary block diagram of a millimeter wave (35-39 GHz) CMOS transceiver.

The methods of the present disclosure utilize MMWs because of their advantage over other ranges of the spectrum in detecting changes in glucose levels. For example, optical techniques (in the optical range of electromagnetic spectrum) that measure amplitude transmission through the skin from a single frequency laser diode source are not as sensitive as MMW techniques. In fact, the MMW band has a natural sensitivity to very small changes in index of refraction (real and imaginary) of fluids, and by a natural coincidence these changes are strongly coupled to glucose levels in the blood and in tissue. Glucose changes of only a few percent can be detected as a shift in the magnitude and phase of the transmitted microwave power. Unlike in the optical regime, the index of refraction of blood and tissue at MMW frequencies is quite high and small shifts can be easily detected using simple transmitter and receiver circuits. In addition, compact antennas or waveguide structures can be used to direct and focus the microwave energy directly into the tissue and directly towards the detector, unlike the optical range techniques. With MMWs, it is also possible to adjust the frequency to enhance the signal to noise ratio through decreased absorption or through increased volume of tissue being sampled. Due to the long wavelengths at MMW range, there is much less scattered energy than in the optical or infrared ranges, allowing more consistent measurements over time. Finally, MMWs (unlike optical and infrared techniques) can operate at very low exposure levels, well below the safe limit, continuously and with a low RF duty cycle in order to establish an individual baseline for every person and then look for changes from that baseline. In some embodiments, measurements according to the methods of the present disclosure are carried out over a range of frequencies, so that for each measurement estimating a chemical concentration (such as glucose), a plurality of frequencies are transmitted and measured, and a measurement is carried out at each frequency of the plurality of frequencies in the specified range.

A number of embodiments of the disclosure have been described. Nevertheless, it will be understood that various modifications may be made without departing from the spirit and scope of the present disclosure. Accordingly, other embodiments are within the scope of the following claims. Although the present invention has been described in connection with the preferred embodiments, it is to be understood that modifications and variations may be utilized without departing from the principles and scope of the invention, as those skilled in the art will readily understand. Accordingly, such modifications may be practiced within the scope of the invention and the following claims.

The examples set forth above are provided to those of ordinary skill in the art as a complete disclosure and description of how to make and use the embodiments of the disclosure, and are not intended to limit the scope of what the inventor/inventors regard as their disclosure.

Modifications of the above-described modes for carrying out the methods and systems herein disclosed that are obvious to persons of skill in the art are intended to be within the scope of the following claims. All patents and publications mentioned in the specification are indicative of the levels of skill of those skilled in the art to which the disclosure pertains. All references cited in this disclosure are incorporated by reference to the same extent as if each reference had been incorporated by reference in its entirety individually.

It is to be understood that the disclosure is not limited to particular methods or systems, which can, of course, vary. It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

The references in the present application, shown in the reference list below, are incorporated herein by reference in their entirety.

REFERENCES

1. Wahowiak, L., *Blood glucose meters. What to look for—and what to know.* Diabetes Forecast, 2013. 66 (1): p. 38-47.
2. Sacks, D. B., et al., *Guidelines and recommendations for laboratory analysis in the diagnosis and management of diabetes mellitus.* Diabetes Care, 2011. 34 (6): p. e61-99.
3. Vashist, S. K., *Non-invasive glucose monitoring technology in diabetes management: a review.* Anal Chim Acta, 2012. 750: p. 16-27.
4. Tura, A., *Advances in the development of devices for noninvasive glycemia monitoring: Who will win the race.* NT&M, 2010. 28: p. 33-39.
5. Burmeister, J. J. and M. A. Arnold, *Evaluation of measurement sites for noninvasive blood glucose sensing with near-infrared transmission spectroscopy.* Clin Chem, 1999. 45(9): p. 1621-7.
6. Shimomura, Y. O., JP), *Instrument for noninvasively measuring blood sugar level.* 2009, Nagasaki Prefectural Government (JP): United States.
7. Ruchti, T. L. G., Ariz., US), Blank, Thomas B. (Chandler, Ariz., US), Lorenz, Alexander D. (Chandler, Ariz., US), Monfre, Stephen L. (Gilbert, Ariz., US), Hazen, Kevin H. (Gilbert, Ariz., US), Thennadil, Suresh N. (New Castle upon Tyne, GB), *Indirect measurement of tissue analytes through tissue properties.* 2006, Sensys Medical, Inc. (Chandler, Ariz., US): United States.
8. Kottmann, J., et al., *Glucose sensing in human epidermis using mid-infrared photoacoustic detection.* Biomed Opt Express, 2012. 3 (4): p. 667-80.
9. Guo, X., A. Mandelis, and B. Zinman, *Noninvasive glucose detection in human skin using wavelength modulated differential laser photothermal radiometry.* Biomed Opt Express, 2012. 3 (11): p. 3012-21.
10. Yoo, E. H. and S. Y. Lee, *Glucose biosensors: an overview of use in clinical practice.* Sensors (Basel), 2010. 10 (5): p. 4558-76.
11. Kim, D.-K., et al., *Device for the non-invasive measurement of blood glucose concentration by millimeter waves and method thereof.* 2008, Samsung Electronics Co.: USA.
12. Hofmann, M., et al. *A novel approach to non-invasive blood glucose measurement based on RF transmission.* in *IEEE MeMeA.* 2011.
13. Hofmann, M., et al. *Non-invasive glucose monitoring using open electromagnetic waveguides.* in *Eur Microwave Conf.* 2012.
14. Hofmann, M., et al., *Microwave-Based Noninvasive Concentration Measurements for Biomedical Applications.* IEEE Trans Microwave Theory Tech, 2013. 61 (5): p. 2195-2204.

15. Yun, F., et al. *Testing glucose concentration in aqueous solution based on microwave cavity perturbation technique*. in *Int Conf Biomed Eng Inform.* 2010.
16. Qing, W., et al. *Measuring glucose concentration by microwave cavity perturbation and DSP technology*. in *Int Conf Biomed Eng Inform.* 2010.
17. Kim, S., et al., *Noninvasive in vitro measurement of pig-blood d-glucose by using a microwave cavity sensor.* Diabetes Res Clin Pract, 2012. 96 (3): p. 379-84.
18. Melikyan, H., et al., *Non-invasive in vitro sensing of D-glucose in pig blood.* Med Eng Phys, 2012. 34 (3): p. 299-304.
19. Dobson, R., R. Wu, and P. Callaghan, *Blood glucose monitoring using microwave cavity perturbation.* Electron Lett, 2012. 48 (15): p. 905-906.
20. Gennarelli, G., et al., *A Microwave Resonant Sensor for Concentration Measurements of Liquid Solutions.* Sensors Journal, IEEE, 2013. 13 (5): p. 1857-1864.
21. Sharma, N. K. and S. Singh. *Designing a non invasive blood glucose measurement sensor.* in *IEEE ICIIS.* 2012.
22. Topsakal, E., T. Karacolak, and E. C. Moreland. *Glucose-dependent dielectric properties of blood plasma.* in *General Assembly and Scientific Symposium, 2011 XXXth URSI.* 2011.
23. Bababjanyan, A., et al., *Real-time noninvasive measurement of glucose concentration using a microwave biosensor.* Journal of Sensors, 2010. 2010.
24. Schwerthoeffer, U., et al. *A microstrip resonant biosensor for aqueous glucose detection in microfluidic medical applications.* in *Biomedical Wireless Technologies, Networks, and Sensing Systems (BioWireleSS), 2014 IEEE Topical Conference on.* 2014. IEEE.
25. Nikawa, Y. and D. Someya. *Non-invasive measurement of blood sugar level by millimeter waves.* in *Microwave Symposium Digest, 2001 IEEE MTT-S International.* 2001. IEEE.
26. Garcia, H. C., et al. *Glucose sensing in saline solutions using V-band waveguides.* in *Wireless Mobile Communication and Healthcare (Mobihealth), 2014 EAI 4th International Conference on.* 2014.
27. Dhakal, R., et al., *Complex permittivity characterization of serum with an air-bridge enhanced capacitor for quantifiable detection of glucose.* Applied Physics Letters, 2015. 106 (7): p. 073702.
28. Afroz, S., et al. *Implantable SiC based RF antenna biosensor for continuous glucose monitoring.* in *SENSORS, 2013 IEEE.* 2013.
29. Chretiennot, T., D. Dubuc, and K. Grenier. *Double stub resonant biosensor for glucose concentrations quantification of multiple aqueous solutions.* in *Microwave Symposium (IMS), 2014 IEEE MTT-S International.* 2014.
30. Al-shamma'a, A. L., GB), Mason, Alex (Liverpool, GB), Shaw, Andrew (Liverpool, GB), Non-Invasive *Monitoring Device.* 2012, AL-SHAMMA'A AHMED, MASON ALEX, SHAW ANDREW: United States.
31. Hancock, C. P. B. N. E. S., GB), Apparatus and method for measuring constituent concentrations within a biological tissue structure. 2014, Credent Medical Limited (Liverpool, GB): United States.
32. Fischer, G. N., DE), *Armband for a Detection Device for the Detection of a Blood Count Parameter.* 2013, Friedrich-Alexander-Universitaet Erlangen-Nuernberg (Erlangen, DE), eesy-id GmbH (Graefelfing, DE): United States.
33. Schrepfer, T. W. O., CH), Caduff, Andreas (Zürich, CH), Hirt, Etienne (Cham, CH), Süsstrunk, Heinz (Zürich, CH), *Method and device for determining the concentration of a substance in body liquid.* 2010, Solianis Holding AG (Zug, CH): United States.
34. IEEE, *IEEE Standard for Safety Levels With Respect to Human Exposure to Radio Frequency Electromagnetic Fields,* 3 kHz to 300 GHz. IEEE Std C95.1-2005, ed. C.-K. Chou and J. D'Andrea. 2005, Piscataway, N.J.: IEEE. 1-238.
35. Karacolak, T., E. C. Moreland, and E. Topsakal, *Cole-cole model for glucose-dependent dielectric properties of blood plasma for continuous glucose monitoring.* Microw Opt Technol Lett, 2013. 55 (5): p. 1160-1164.
36. Siegel, P. H., Y. Lee, and V. Pikov. *Millimeter-wave non-invasive monitoring of glucose in anesthetized rats.* in *Infrared, Millimeter, and Terahertz waves (IRMMW-THz), 2014 39th International Conference on.* 2014. IEEE.

What is claimed is:

1. A device for in vivo transdermal blood glucose concentration measurement, the device comprising:
    a clip having a first pad and a second pad;
    an electromagnetic wave transmitter with a first directional antenna that comprises a flexible polymer substrate and a flexible metallic pattern situated on the first pad, the electromagnetic wave transmitter configured to be attached to one side of a biological tissue containing blood vessels and transmit electromagnetic waves through the biological tissue;
    an electromagnetic wave receiver with a second directional antenna that comprises a flexible polymer substrate and a flexible metallic pattern situated on the second pad, the electromagnetic wave receiver configured to be attached to an opposite side of the biological tissue from the electromagnetic wave transmitter and to receive the electromagnetic waves transmitted through a fixed thickness of the biological tissue; and
    an electromagnetic wave analyzer configured to measure transmittance of the electromagnetic waves and analyze the electromagnetic waves before or after transmission for changes in magnitude and phase of the electromagnetic waves,
    wherein:
    the device is configured to estimate, continuously over at least a 24-hour period, a chemical concentration of glucose or a change in the chemical concentration of glucose in the biological tissue, based on an inverse proportionality between the chemical concentration of glucose and an absorption of the electromagnetic waves through the fixed thickness of the biological tissue or a direct proportionality between the chemical concentration of glucose and a transmittance of the electromagnetic waves through the fixed thickness of the biological tissue,
    the biological tissue is either a human ear lobe having a thickness of 1 mm or more or a human skin fold between fingers having a thickness of 1 mm or more,
    the device is configured to tune within a range of frequencies between 27 to 40 GHz of the electromagnetic waves in order to enhance the signal-to-noise ratio for permittivity and absorption loss for a particular subject or application without changing geometries of said first directional antenna and said second directional antenna and also without changing placements of said first directional antenna and said second directional antenna,
    a distance between the first directional antenna and the second directional antenna is between one and two wavelengths of the electromagnetic wave, and the estimate is based on averaging over a range of frequencies.

2. The device of claim 1, further comprising a display for displaying results from the electromagnetic wave analyzer.

3. The device of claim 2, wherein the electromagnetic wave transmitter is configured to modulate, and the electromagnetic wave receiver is configured to detect, a magnitude and phase of the electromagnetic waves.

4. The device of claim 1, wherein the electromagnetic wave transmitter comprises an electromagnetic wave source selected from the group consisting of: a backward-wave oscillator, an orotron, a Gunn diode oscillator, an IMPATT diode, a solid state Gunn diode, a synthesizer with upconverter, an oscillator and discrete amplifier, a MMIC amplifier, a silicon or silicon germanium CMOS oscillator and power amplifier, a YIG tuned oscillator, a dielectric resonator, a vacuum tube oscillator, a clinotron, a gyro-klystron, a gyrotron, a traveling wave tube, a gyro-traveling wave tube, and a pulsed magnetron.

5. The device of claim 4, wherein the first directional antenna comprises a flexible polymer substrate.

6. The device of claim 5, wherein the flexible polymer substrate is selected from the group consisting of: polyimide, LCP, polytetrafluoroethylene, SU-8 photoresist, polyethylene, polypropylene, TPX, polystyrene, and parylene.

7. The device of claim 6, wherein the first directional antenna further comprises a flexible metallic pattern.

8. The device of claim 1, further comprising an electromagnetic beam shaping element between the electromagnetic wave transmitter and the biological tissue.

9. The device of claim 8, wherein the electromagnetic beam shaping element is selected from the group consisting of: a convex lens, a concave lens, a collimating lens, a spherical mirror, a parabolic mirror, an elliptical mirror, and a conical mirror.

10. The device of claim 1, wherein a distance between the electromagnetic wave transmitter and receiver is less than one wavelength of the electromagnetic wave.

11. The device of claim 1, wherein the fixed distance between the electromagnetic wave transmitter and receiver is between one and two wavelengths of the electromagnetic wave.

12. A method of in vivo transdermal blood glucose concentration measurement, the method comprising:
providing a clip having a first pad and a second pad opposite the first pad, the first pad comprising a first directional antenna that comprises a flexible polymer substrate and a flexible metallic structure and the second pad comprising a second directional antenna that comprises a flexible polymer substrate and a flexible metallic structure;
clipping the clip to opposing sides of a biological tissue containing blood vessels, the biological tissue being either a human ear lobe having a thickness of 1 mm or more or a human skin fold between fingers having a thickness of 1 mm or more;
i) applying, by the first directional antenna, electromagnetic waves at a frequency in the range of 20 to 300 GHz to the biological tissue,
ii) receiving, by the second directional antenna, the electromagnetic waves transmitted through the biological skin fold;
iii) analyzing the received electromagnetic waves for changes in transmittance magnitude or phase;
iv) estimating a chemical concentration or a change in the chemical concentration in the biological tissue, based on the analyzed electromagnetic waves averaged over a range of frequencies, wherein:
the chemical concentration is of blood glucose, and is estimated based on an inverse proportionality between the chemical concentration of blood glucose and absorption of the electromagnetic waves or a direct proportionality between the chemical concentration of glucose and the transmittance of the electromagnetic waves, and
the step of applying the electromagnetic waves is performed by an electromagnetic wave transmitter comprising an electromagnetic wave source and the first directional antenna; and
v) diagnosing or monitoring metabolic disorders of carbohydrate metabolism characterized by hyperglycemia or hypoglycemia or monitoring changes in carbohydrate metabolism in response to a diet or activity pattern, based on the blood glucose concentration,
wherein step v) is performed continuously over at least a 24-hour period by continuously performing, over the at least 24-hour period, steps i)-iv),
wherein steps i)-iv) comprise tuning a frequency in the range of 27 to 40 GHz of the electromagnetic waves in order to enhance the signal-to-noise ratio for a particular subject or application without changing geometries of said first directional antenna and said directional second antenna and also without changing placements of said first directional antenna and said second directional antenna,
and
a distance between the first directional antenna and the second directional antenna is between one and two wavelengths of the electromagnetic wave.

13. The method of claim 12, wherein applying electromagnetic waves comprises applying electromagnetic waves at different frequencies, at different amplitudes, and at different modulation rates.

14. The method of claim 12, wherein the step of applying the electromagnetic waves comprises applying the electromagnetic waves in a duty cycled manner.

15. The method of claim 12, wherein the metabolic disorder is diabetes mellitus.

16. The method of claim 15, wherein the biological skin fold is an ear, neck, arm, or leg.

17. The method of claim 12, wherein the electromagnetic wave source is selected from the group consisting of: a backward-wave oscillator, an orotron, a Gunn diode oscillator, an IMPATT diode, a solid state Gunn diode, a synthesizer with upconverter, an oscillator and discrete amplifier, a MMIC amplifier, a silicon or silicon germanium CMOS oscillator and power amplifier, a YIG tuned oscillator, a dielectric resonator, a vacuum tube oscillator, a clinotron, a gyro-klystron, a gyrotron, a traveling wave tube, a gyro-traveling wave tube, and a pulsed magnetron.

18. The method of claim 17, wherein the first directional antenna comprises a flexible polymer substrate selected from the group consisting of: polyimide, LCP, polytetrafluoroethylene, SU-8 photoresist, polyethylene, polypropylene, TPX, polystyrene, and parylene.

19. The method of claim 18, wherein the first directional antenna is fabricated by nanoimprint lithography, optical lithography, electron beam lithography, X-ray lithography, or synchrotron radiation etching.

20. The method of claim 19, wherein the first directional antenna further comprises a flexible metallic structure, the metallic structure fabricated by electroplating, liftoff, spinning, plasma etching, or sputter deposition.

21. The method of claim 16, wherein the step of applying the electromagnetic waves further comprises applying an electromagnetic beam shaping element between the electromagnetic wave transmitter and the biological skin fold.

22. The method of claim 21, wherein the electromagnetic beam shaping element is selected from the group consisting of: a convex lens, a concave lens, a collimating lens, a spherical mirror, a parabolic mirror, an elliptical mirror, and a conical mirror.

23. The method of claim 12, further comprising:
monitoring over at least seven days an individual's absorption signature of the electromagnetic waves, based on the step of estimating the chemical concentration or change in the chemical concentration;
evaluating normal day-to-day variability for the individual's absorption signature, based on the step of monitoring the individual's absorption signature;
correlating levels of the chemical concentration directly with an absolute value for the individual; and
evaluating changes in the chemical concentration deviating from normal chemical concentration levels, based on the steps of monitoring the individual's absorption signature, evaluating the normal day-to-day variability of the individual's absorption signature, and correlating levels of the chemical concentration with an absolute value for the individual.

24. The method of claim 23, wherein the absolute value is determined through a blood test.

25. The method of claim 12, wherein the step of applying the electromagnetic waves at a frequency in the range of 27 to 40 GHz comprises applying the electromagnetic waves at a plurality of frequencies for each estimating.

26. The method of claim 23, wherein the step of evaluating changes is in response to a change in a diet or activity pattern.

27. The method of claim 12, wherein the step of applying the electromagnetic waves at a frequency in the range of 27 to 40 GHz comprises the frequency being in a range of 35 to 39 GHz.

28. The method of claim 12, wherein the step of applying the electromagnetic waves at a frequency in the range of 27 to 40 GHz comprises the frequency being in a range of 33 to 37 GHz.

* * * * *